(12) United States Patent
Dasch

(10) Patent No.: US 7,021,143 B2
(45) Date of Patent: Apr. 4, 2006

(54) CYLINDRICALLY-ROTATING ULTRASONIC PHASED ARRAY INSPECTION METHOD FOR RESISTANCE SPOT WELDS

(75) Inventor: Cameron J. Dasch, Bloomfield Hills, MI (US)

(73) Assignee: General Motors Corporation, Detroit, MI (US)

( * ) Notice: Subject to any disclaimer, the term of this patent is extended or adjusted under 35 U.S.C. 154(b) by 0 days.

(21) Appl. No.: 10/733,720

(22) Filed: Dec. 11, 2003

(65) Prior Publication Data

US 2005/0126293 A1   Jun. 16, 2005

(51) Int. Cl.
*G01N 29/26* (2006.01)

(52) U.S. Cl. .......................................... 73/620; 73/644
(58) Field of Classification Search .................. 73/618, 73/620, 625, 626, 644; 600/444, 445
See application file for complete search history.

(56) References Cited

U.S. PATENT DOCUMENTS

| 3,936,791 | A |   | 2/1976  | Kossoff         |         |
|-----------|---|---|---------|-----------------|---------|
| 4,208,917 | A | * | 6/1980  | Aoyama et al.   | 73/644  |
| 4,455,872 | A | * | 6/1984  | Kossoff et al.  | 73/618  |
| 5,333,612 | A | * | 8/1994  | Wild            | 600/445 |
| 5,503,152 | A |   | 4/1996  | Oakley et al.   |         |
| 5,846,205 | A |   | 12/1998 | Curley et al.   |         |
| 5,865,751 | A |   | 2/1999  | Okuno et al.    |         |
| 6,344,739 | B1|   | 2/2002  | Hardy et al.    |         |

* cited by examiner

*Primary Examiner*—John E. Chapman
(74) *Attorney, Agent, or Firm*—Kathryn A. Marra (57) ABSTRACT

The present invention provides an ultrasonic inspection assembly having an ultrasonic transducer mounted on a stage, with a support structure below. The support structure is coupled to the stage, and the support structure has an interior space filled with a couplant media. The transducer is oriented such that it transmits ultrasonic waves through the media. A drive mechanism rotates one of the stage and the support structure relative to the other one of the stage and the support structure.

15 Claims, 4 Drawing Sheets

CYLINDRICALLY-ROTATING ULTRASONIC PHASED ARRAY INSPECTION METHOD FOR RESISTANCE SPOT WELDS

FIELD OF THE INVENTION

The present invention relates to non-destructive physical inspection, and more particularly to ultrasonic testing devices and methods therefor.

BACKGROUND OF THE INVENTION

Resistance spot welding (RSW) is used for the fabrication of sheet metal assemblies. The process is used to join low carbon steel components by applying a potential across two electrodes connected to the respective components. High-strength low-alloy steel, stainless steel, nickel, aluminum, titanium and copper alloys are also frequently spot welded. RSW is used in a variety of applications including automotive welding of the bodies and chassis of automobiles, trucks, trailers, buses, mobile homes, motor homes and recreational vehicles, as well as for joining cabinets, office furniture, appliances and many other products.

Resistance spot welding can be performed at high speeds and is particularly useful for automated high rate production assemblies. However, due to the complexity of the basic process, RSW potentially produces inconsistent weld quality. Previous methods of quality control testing have traditionally revolved around destructive testing to physically inspect the weld integrity. Such destructive testing completely destroys the workpiece, and wastes both resources and materials, especially in large volume production operations. Pry or "chisel" tests which distort the metal are also used. Although ultrasonic non-destructive testing of RSW is known, previously it has not been used with great success due to requirements for highly trained operators, manual dexterity, weld material dependences, and cost.

Thus, ensuring weld quality has been and remains a major challenge and goal. There is a need for an ultrasonic testing apparatus that provides a fast, reliable, high quality method of inspecting small target areas, which is neither cost prohibitive nor operator dependent.

SUMMARY OF THE INVENTION

The present invention provides an ultrasonic inspection assembly comprising an ultrasonic transducer that is mounted on a stage. The assembly comprises a support structure having a proximal end adjacent to the stage and a terminal end opposite to the stage, the support structure defining an interior space filled with a media which transmits ultrasonic waves. The stage and the proximal end of the support structure are coupled to one another. The transducer is oriented such that it transmits ultrasonic waves through the media. The assembly comprises a drive mechanism for rotating one of the stage and the support structure relative to the other one of the stage and the support structure.

Alternate preferred embodiments of the present invention comprise an ultrasonic inspection assembly for testing resistance spot welds comprising a high frequency linear phased array ultrasonic transducer mounted on a stage. The assembly comprises a support structure having a proximal end adjacent to the stage and a terminal end opposite to the stage, which is in contact with a resistance spot weld target. The support structure defining an interior space filled with a media which transmits ultrasonic waves. The transducer is arranged to direct ultrasonic waves through the media to the spot weld target. The stage and the proximal end of the support structure are coupled to one another. The assembly also comprises a drive mechanism for rotating the stage relative to the support structure.

The present invention further comprises a method for non-destructive ultrasonic testing comprising positioning an ultrasonic detection assembly over a target, contacting a terminal end of the detection assembly with a surface of the target, activating an ultrasonic transducer to transmit ultrasonic waves through the proximal end to the target, registering any ultrasonic waves reflected from the target to the transducer, and moving the transducer relative to the proximal end to reposition the transducer.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

The present invention relates to non-destructive ultrasonic inspection for characterizing solid or target surfaces, including a method of inspection and an inspection assembly. The present invention is particularly well suited for the non-destructive testing for integrity of resistance spot welds. Preferred embodiments of the present invention provide an assembly for ultrasonic diagnostics or inspection which comprises a stage positioned over a support structure. The support structure has an internal space which is filled with a media conducive to transmitting ultrasonic waves (i.e. a couplant media) such as water, for example. An ultrasonic transducer is mounted onto the stage to confront a proximal end of the support structure and is oriented such that it transmits ultrasonic waves through the media. An opposite terminal end of the support structure is positioned proximate to (and preferably contacting) a target which is to be tested by subjecting it to the emitted ultrasonic waves. The stage and the support structure are attached to one another by a coupling, such as a retaining ring or fastener(s) or both. A drive mechanism rotates one of the stage and the support structure relative to the other one of the stage and the support structure. In certain preferred embodiments, the stage rotates relative to the support structure. Further, for applications where the target is a resistance spot weld, it is preferred that the ultrasonic transducer is a high frequency linear phased array ultrasonic transducer. Preferred embodiments of the present invention will be described in more detail below.

A number of scanning and image display techniques have become generally standardized for ultrasonic inspection. These include the "A-scan", wherein a focused or "pencil" beam is directed into the object of interest. The reflected energy, that is, "echoes" are detected and displayed, by a "trace" plotting the amplitude of the received energy signal on the vertical axis and time after transmission on the horizontal axis, such that the distance of features in the trace from one edge of the display indicates the relative depth of the reflecting interfaces.

Structural information about the material being inspected can be obtained by collecting A-scans at a series of proximal points and combining them to form a "B-scan", where a two-dimensional image, i.e., an image of a cross-sectional "slice" is formed. An elongated multiple-element transducer is commonly used to provide a series of parallel "pencil" beams focused by sequential addressing, phase or physical steering techniques. "Lines" corresponding to energy reflected from the elements along the path of successive pencil beams extending into a particular portion of the target object are displayed side-by-side, while the brightness of the display is varied responsive to the strength of the reflected signal. The images formed each correspond to a cross-sectional view or two-dimensional "slice" extending into the object to be imaged.

Most ultrasonic imaging creates as thin a cross-sectional "slice" as possible, through the target of interest. The thickness of the slice limits the resolution of the image. "B-scan" ultrasonic imaging techniques can be further enhanced by scanning over an area to collect enough images for generating a three-dimensional image. Preferably, a plurality of different positions of cross-sections, or slices, are taken to generate a comprehensive three-dimensional image.

The elements or individual transducers in an array are arranged to emit ultrasonic energy in a generally diverging, wedge-shaped pattern, so that any given region of the object to be examined is "illuminated" with energy from elements in each of the arrays. Transducer elements are typically formed of a piezoelectric material, and are configured and operated to emit a beam of ultrasonic energy of desired beam shape when excited by suitable high-frequency electrical signals. The same elements (or adjoining elements of generally similar material and configuration) provide electrical signals responsive to detection of echoes that is responsive to detection of ultrasonic energy after reflection at interfaces between materials of differing acoustic impedance within an object the internal structure of which is to be imaged.

Any ultrasonic transducer may be employed with the present invention. In preferred embodiments, a linear phased array transducer is selected as the ultrasonic transducer. Such linear phased array ultrasonic transducers only generate a scan of single slice of the target. For successful inspection, the linear array ultrasonic transducer assembly must be mechanically translated in order to sufficiently scan and cover a target area. Further, when the features to be detected over a target area are relatively small, better imaging is obtained by higher frequency ultrasonic transducers. In optimizing the design of assemblies incorporating such linear phased arrays, it is preferred to make them as small, light, robust, and sealable as possible. In particularly preferred embodiments, where the testing is for resistance spot welds the preferred method of scanning is taking a series of linear scans or slices at a variety of positions of differing rotational angles with a high frequency linear phased array ultrasonic transducer. Previously, such scanning has only been done in a translational manner, taken along an axis perpendicular to the array axis and parallel to the surface to be inspected. One preferred aspect of the present invention is the ability to rotate the transducer array, while keeping the remaining parts of the assembly stationary (i.e. the support structure) without any need for physical translation, in multiple directions, as discussed further below.

Figure 1:
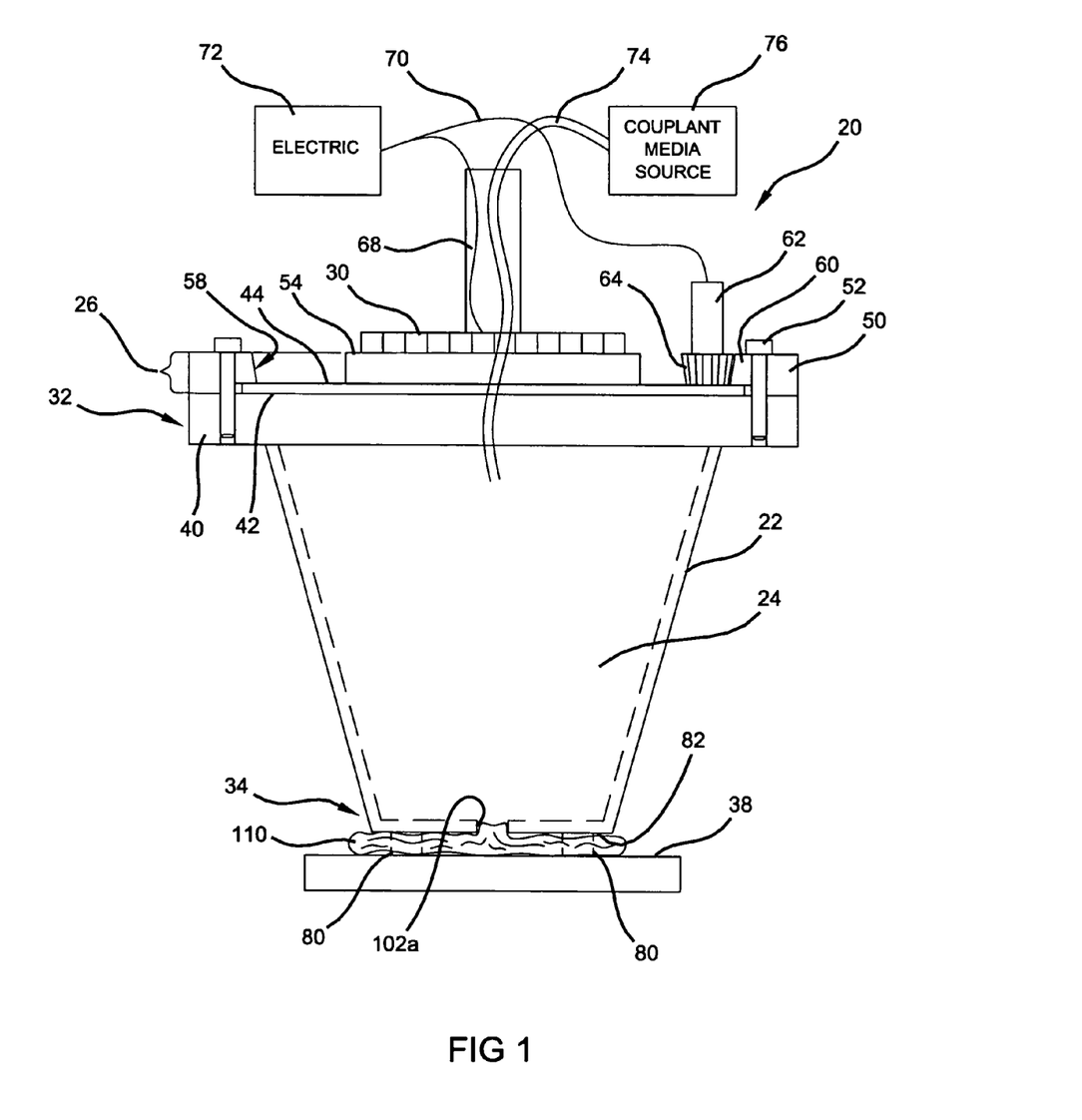
FIG. 1 is a schematic view of a preferred embodiment of the present invention having a horizontal sealing configuration and an aperture at a terminal surface for continuous wetting of a target with couplant media.

An ultrasonic inspection assembly 20 according to the present invention is shown in FIG. 1. The assembly 20 comprises a support structure 22 defined by an interior space 24. A stage 26 is disposed above the support structure 22. A linear phased array ultrasonic transducer 30 is attached to the stage 26. The support structure 22 has a proximal end 32 and a terminal end 34. The proximal end 32 is adjacent to the stage 26, and the terminal end 34 is adjacent to a surface of a target 38 to be tested and/or diagnosed by the ultrasonic assembly 20. The support structure 22 defines an open interior space 24. The cavity of the interior space 24 is fully filled with a couplant media source (not shown) which is conducive to propagating ultrasonic waves without unduly interfering with the operation of the ultrasonic transducer 30 attached to the stage 26.

In the present embodiment as shown, a horizontal sealing configuration is shown. The proximal end 32 of the support structure 22 terminates in a circumferential lip or collar 40 having an upper horizontal surface 42 which contacts the stage 26. The stage 26 comprises a sealing flange plate 44 that contacts the collar 40, and preferably provides fluid-tight contact with the collar 40 to prevent fluid communication therebetween.

The support structure 22 and stage 26 are attached to one another by any coupling known to be suitable to the present invention by skilled artisans. As shown the coupling comprises a retaining ring 50 that fits around the circumference of the flange 44 of the stage 26 and the collar 40 of the support structure 22. Fasteners, such as bolts 52 (as shown) or rivets, may further attach the retaining ring 50 to the collar 40. The stage 26 further comprises the ultrasonic transducer 30, attached to the flange 44 by a potting material 54. An interior circumference 58 of the retaining ring 50 comprises a gear ring 60. A drive mechanism, such as a drive motor 62, is attached to a pinion gear 64, which traverses along the gear ring 60 to provide rotational translation of the stage 26 relative to a stationary support structure 22.

An umbilical cable 68 is shown attached to the stage 26. The umbilical cable 68 houses an electrically conductive conduit 70 which connects a power supply 72 to the transducer 30 and to the drive motor 62. Further the umbilical cable 68 may also contain a couplant media supply line 74 connected to a couplant media supply source 76, in the case where couplant media must be replenished within the interior area 24 of the support structure 22, as will be discussed in more detail below.

At the terminal end 34 of the support structure 22, support legs 80 are disposed on a terminal surface 82 of the support structure 22. The support legs 80 position and suspend the assembly 20 over the target surface 38 and protect the surface 38 and the assembly 20 from any potential damage. The terminal surface 82 of the support structure 22 at the terminal end 34 is preferably at least partially comprised of flexible or elastic material that may protrude while under the head pressure exerted by the couplant media within the interior space 24 of the support structure 22. Thus, in preferred embodiments, the terminal surface 82 protrudes to the extent that it contacts the target surface 38 and provides an enhanced interface for testing the target with ultrasonic waves.

Figure 2:
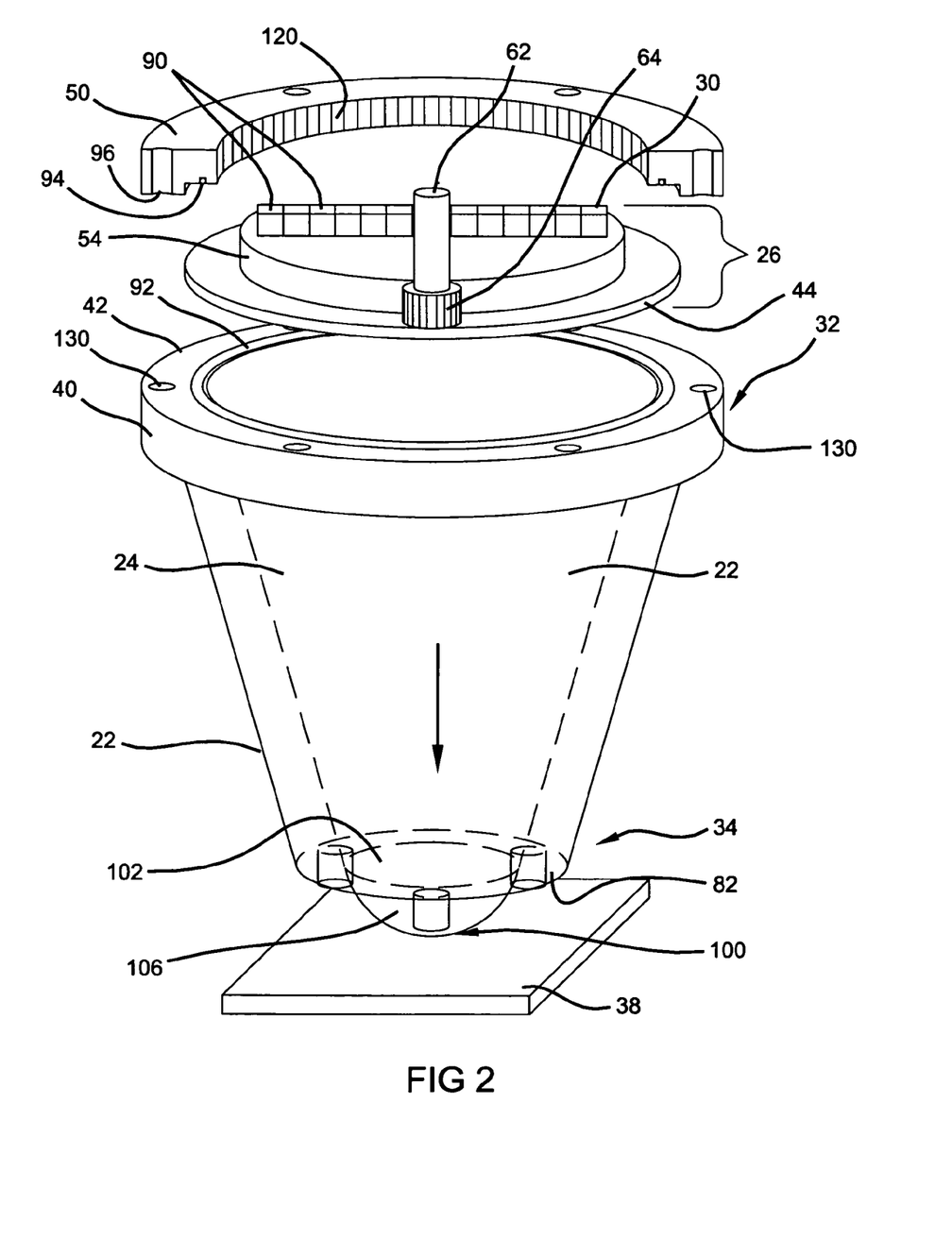
FIG. 2 is a partial detailed schematic view of another preferred embodiment of the present invention having a horizontal sealing configuration and an impermeable diaphragm at a terminal surface.

A more detailed view of an alternate preferred embodiment of the present invention is shown in FIG. 2. The stage 26 is positioned over the support structure 22 at the proximal end 32, and comprises the flange 44 on which the linear phased array ultrasonic transducer 30 is mounted. The transducer 30 comprises a plurality of elements 90 and is attached to the flange 44 by the potting material 54 that provides a solid fluid seal which serves to position and affix the transducer 30 in the desired location. In preferred embodiments of the present invention, the transducer 30 is in direct contact with the coupling media in the interior space 24. The flange 44 contacts the upper horizontal surface 42 of the collar 40 of the support structure 22. In preferred embodiments of the present invention, a fluid-tight seal is formed between the stage 26 and the support structure 22. In the embodiment as shown, the collar 40 portion of the support structure 22 has a circular hollow channel which circumscribes the entire collar 40 and in which a lower O-ring 92 is disposed, which prevents fluid communication between the interior space 24 of the support structure 22 through the flange 44 to an exterior of the assembly 20. However, any configuration of seals in conceivable with the present invention, which prevents fluid communication between the interior space 24 and the exterior of the assembly 20. The number and configuration of seals is dependent upon the type of coupling media employed with the present invention, and may vary, as recognized by one of skill in the art.

The interior space 24 of the support structure 22 preferably has a tapered cylindrical shape to accommodate the phased array transducer 30 at the proximal end 32, while optimizing the distance and shape of the ultrasonic beams emitted from the transducers 30. The larger circumference at the proximal end 32 coincides with the size of the phased array transducer 30, which is generally the largest component within the assembly 20. The smaller circumference of the support structure 22 is at the terminal end 34 and is optimally as small as possible, to permit the assembly 20 and terminal surface 82 to navigate into tight, small, and/or narrow areas for inspection, while still maintaining a sufficient terminal surface 82 area to interface with the target objects. The distance of the support structure 22 measured from the proximal to the terminal end 32,34 generally coincides to the optimum distance between the transducer 30 and target to minimize this distance and the size of the apparatus while adequately focusing the beam on the target area 38.

The features relevant to determining the optimal distance are known to those skilled in the art. If the overall distance is too short, the beam is very tightly focused and diverges quickly. The collimated distance at the focus is called the "working distance." If the water-column distance is too large, the probe becomes very large and unwieldy and the focal spot size increases. A distance of between about 15 mm to about 30 mm is a preferred distance for the transducers 30 in the assembly 20 of the present invention. Ideally, in all cases of transducers, the working distance needs to be at least twice the maximum thickness of the object to be inspected. If ultrasonic beam attenuation is used to evaluate the weld, the working distance should be at least three times the weld thickness to allow at least two back wall reflections while traversing essentially the same volume.

The length of the array and hence the diameter of the device should be large enough to include inspection material outside the weld nugget. This provides reference areas outside of the welded material to ensure proper probe alignment. Additional area is also needed for multi-element phased array beam generation. To cover a length of at least 20 mm, the total transducer size is generally around 25 mm at the proximal end 32 of the support structure 22.

The materials of construction of the support structure 22 may include either opaque or transparent materials. Transparent materials may provide advantages in positioning the assembly 20 over the target area 38, where necessary. Any durable material of construction that is chemically compatible with the couplant media contained within the interior space 24. Preferred materials include stainless steel, brass, or lightweight plastics, such as acrylics, polyesters, phenolics, epoxies, polycarbonates, polystyrene, polypropylene, nylon, and the like. Materials of construction for the flange 44 of the stage 26 also may be any material compatible with the selected couplant media, and are preferably lightweight, such as the plastics used for the support structure 22.

According to the present invention, it is preferred to minimize the size and weight of the ultrasonic inspection assembly 20, while optimizing the quality of the three-dimensional images produced. Various factors are used to optimize the design of the assembly 20 which revolves around transducer 30 selection. Such factors considered in ultrasonic transducer 30 selection include: cost, ultrasonic frequency of the transducer 30, transducer 30 to surface 38 distance, total number of transducer elements 90, element-to-element 90 spacing, number of elements 90 fired simultaneously, lateral size of the elements 90, and the use of a cylindrical lens.

As known to those skilled in the art, the width of the array and additional focusing devices will determine the thickness of each image slice. For simplicity and cost, one preferred embodiment includes a one-dimensional (linear) array with elements of about 4 mm lateral width, where a cylindrical lens is placed over the array with the axis of the lens along the scan axis of the linear array. In alternate preferred embodiments, such focusing of the ultrasonic transducer beam output could also be accomplished by using a two-dimensional array with as few as three rows of elements with the outside rows phase-adjusted to focus the beam. However, other arrays (with or without lens) are also suitable for use with the present invention. It is preferred to produce a fairly tight focus region which is collimated through several reflections in the target object, which provides a fairly uniform sampling area for each focal region. Typical resistance spot weld nuggets range from approximately 3.5 mm to 6.5 mm, with sheets having a thickness of between about 0.6 mm to 4.0 mm. Only a modest resolution is needed for this diameter measurement, approximately 15% of the minimum expected size. In such a case, the array should be able to scan an area of about 20 mm, and a depth resolution of approximately 15% of the minimum sheet thickness (e.g. 0.1 mm). Thus, it is preferred for steel that the transducer 30 has a frequency of between 15 to 30 MHz (i.e. high frequency ultrasonic waves) to achieve the needed depth-spatial resolution.

Thus, a preferred ultrasonic transducer suitable for use in ultrasonic imaging of resistance spot welds is a high frequency linear phased array having a frequency of from between about 15 to about 30 MHz or higher. A frequency of higher than about 17 MHz is particularly preferred. For example, one preferred transducer array 30 for use with the present invention has at least 64 elements with a pitch of 0.3 mm, with each element having a length of 3 mm and a cylindrical lens (which is generally preferred), such as the high frequency linear phased arrays commercially available with controllers, such as the Omniscan with PA probes or the TomoScan with PA probes, both available from R/D Tech of Quebec, Canada. The beam is well behaved at a working distance of 25 mm, and thus the support structure has a length of 25 mm corresponding to this working distance. Although the above high frequency linear phased array ultrasonic transducers are not limiting to the applicability of the present invention, the above examples have been found to optimize the size, weight, and cost where the assembly is testing small targets, such as resistance spot welds.

As discussed above, the interior space 24 of the support structure 22 is preferably filled with a couplant media that is conducive to transmitting ultrasonic waves without interference or noise. Ultrasonic waves are strongly attenuated by air, so it is preferred that a liquid or solid coupling medium is disposed between the transducer 30 and the target area 38. Because most solid elastomers also attenuate high frequency ultrasonics, they will be used only as thin membranes or diaphragms. Solid elastomer polymers suitable as couplants are soft hydrophilic polymers and latexs. Water based gels such as sol-gels or polyacrylamide gels are also suitable couplants. A preferred couplant media for the present invention is liquid water. The selection of the couplant media depends upon the selection of the seal configuration at the terminal surface 82 and the abrasiveness of the welds to be inspected.

An interface 100 between the terminal surface 82 and the target object surface 38 may be designed in two preferred alternate embodiments. In the first configuration, shown in FIG. 2, a terminal aperture 102 at the terminal end 34 is sealed by a diaphragm 106 constructed of a flexible or elastic material. The material of the diaphragm 106 is flexible, or compliant, and transparent to ultrasonic waves. One preferred diaphragm material is a latex membrane. The diaphragm 106 prevents fluid communication between the interior and exterior of the support structure 22. It should be noted that with the present configuration, there is no need for continuous supply of couplant media to the assembly 20 during operation, eliminating the need to connect the assembly 20 via a supply conduit connected to a supply source (74 connected to 76 in FIG. 1). Rather, the couplant media may be replenished as necessary during non-operational downtime.

The diaphragm 106 protrudes beneath the terminal surface 82 due to the head pressure exerted by the couplant media within the interior space 24 of the support structure 22. In preferred embodiments where a diaphragm 106 is disposed at the terminal end 34 sealing the terminal aperture 102, the terminal surface 82 protrudes to the extent that it contacts the target surface 38 and provides an enhanced interface 100 by providing substantially continuous coupling medium for testing the target 38 with ultrasonic waves. It is also possible to apply additional couplant media to the exterior of the diaphragm 106 to enhance the interface 100, as needed, during operation.

In a second preferred configuration, as shown in FIG. 1, the terminal aperture 102a is in an open configuration, or an open "dribbler" as is known in the art. The couplant media is slowly and continuously dripped onto the target surface 38 through the open terminal aperture 102a, which is relatively small in diameter for controlling and minimizing couplant flow. In such an embodiment, water or other liquid couplants are preferred as the couplant medium, due to a relatively low viscosity enabling continuous flow. The flow of water provides a couplant medium layer 110 on the target surface 38 which creates the necessary couplant interface 100 with the terminal surface 38. The terminal aperture 102a of the dribbler may be formed in a similar compliant and flexible material membrane, as that described above for the impermeable diaphragm 106 configuration, while allowing for flow of the couplant medium out of the assembly 20 onto the target object surface 38. The umbilical cable 68 attached to the assembly 20, as previously described, replenishes the coupling medium within the interior space 24 of the support structure 22 as the dribbler operates, and is operated in conjunction with a small supply pump (not shown). Although not shown, the aperture 102a may be sealed when the assembly 20 is not in use, by capping or sealing the terminal end 34 and terminal surface 82 with a temporary impermeable layer, such as a plastic cap, as recognized by one of skill in the art.

Figure 3:
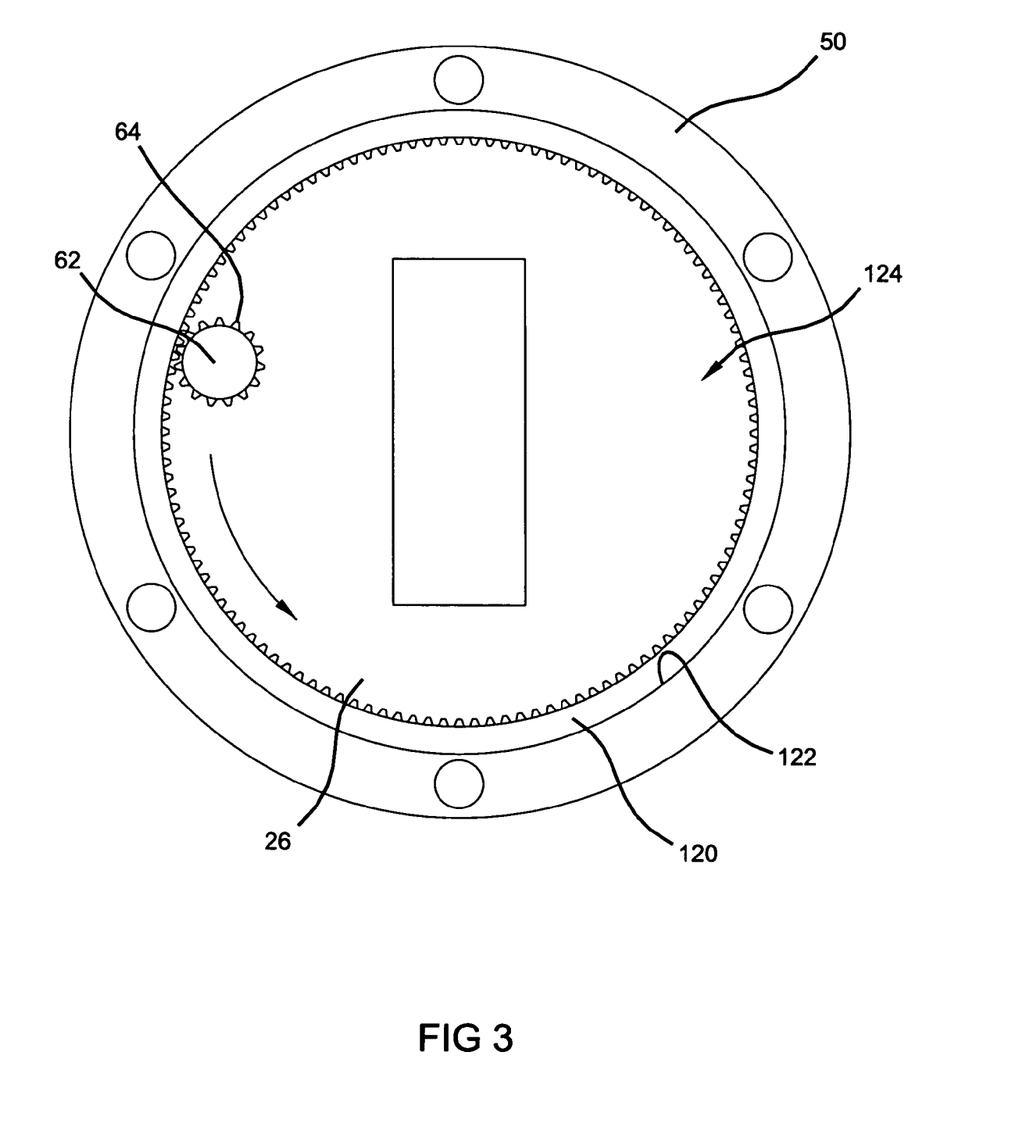
FIG. 3 is a partial overhead schematic view of the embodiment shown in FIG. 2.

As shown in FIGS. 2 and 3 generally, the retaining ring 50 couples the stage 26 to the support structure 22 by clamping them together. The retaining ring 50 further comprises the stationary gear ring 120 along an inner circumference 122 of the retaining ring 50 which interfaces with the pinion gear 64 connected to the drive motor 62 to rotate the stage 26 relative to the support structure 22 beneath, enabling ultrasonic scanning at a variety of rotational positions. The drive motor 62 pinion gear 64 traverses the stationary gear ring 120 at peripheral sides 124 of the stage 26 and thus facilitates rotational movement. Although not depicted, it should be noted that the present invention is equally applicable to an embodiment where the support structure 22 rotates, while the stage 26 is stationary. In such an embodiment, the gear ring would rotate the support structure below, while the stage with the drive motor would not rotate. Another alternate embodiment that is not shown, is where the retaining ring further comprises a protective cap or shroud, that encases the entire stage 26 and its several components. A small aperture would permit the entry of the umbilical cable. Alternatively, the shroud could be attached to the umbilical cord and leave a small gap for the stage 26 to rotate.

Inspection requirements for the target 38 dictate the number of required slicing scans that are needed. For example, with the present invention, the transducer 30 can be rotated and scanned starting at 0°; 45°; 90°; and finally 135°; which in effect scans an entire circular area over the target. Further, according to the present invention the stage 26 needs to rotate only ±90° to achieve a circular span of 180° total while the transducer 30 extends across the diameter of the stage 26 and covers a full 360° sweep. The stage 26 may be rotated to whatever extent necessary by configuring the transducer 30 and stage 26 accordingly, however, it is preferred that rotation is only 180° which allows for a more compact design as the transducer 30 may extend to the perimeter of the flange 44.

The collar 40 may optionally have a plurality of races 130, or channels, for accepting bearings, such as needle bearings or bearing rings, which provide reduced friction when the flange 44 rotates against the stationary retaining ring 50 and collar 40. Additional races may optionally be located within the retaining ring 50, as shown at 94 and 96, to accept additional bearings, such as for example, ball, needle, or ring bearings, to further reduce frictional wear. Further, the bearings serve to center the position of the motor head 62 and pinion gear 64. The retaining ring 50 may also have various fasteners (52 of FIG. 1) that extend through or over the collar 40 to secure the retaining ring 50 to the collar 40 (see FIG. 1).

Figure 4:
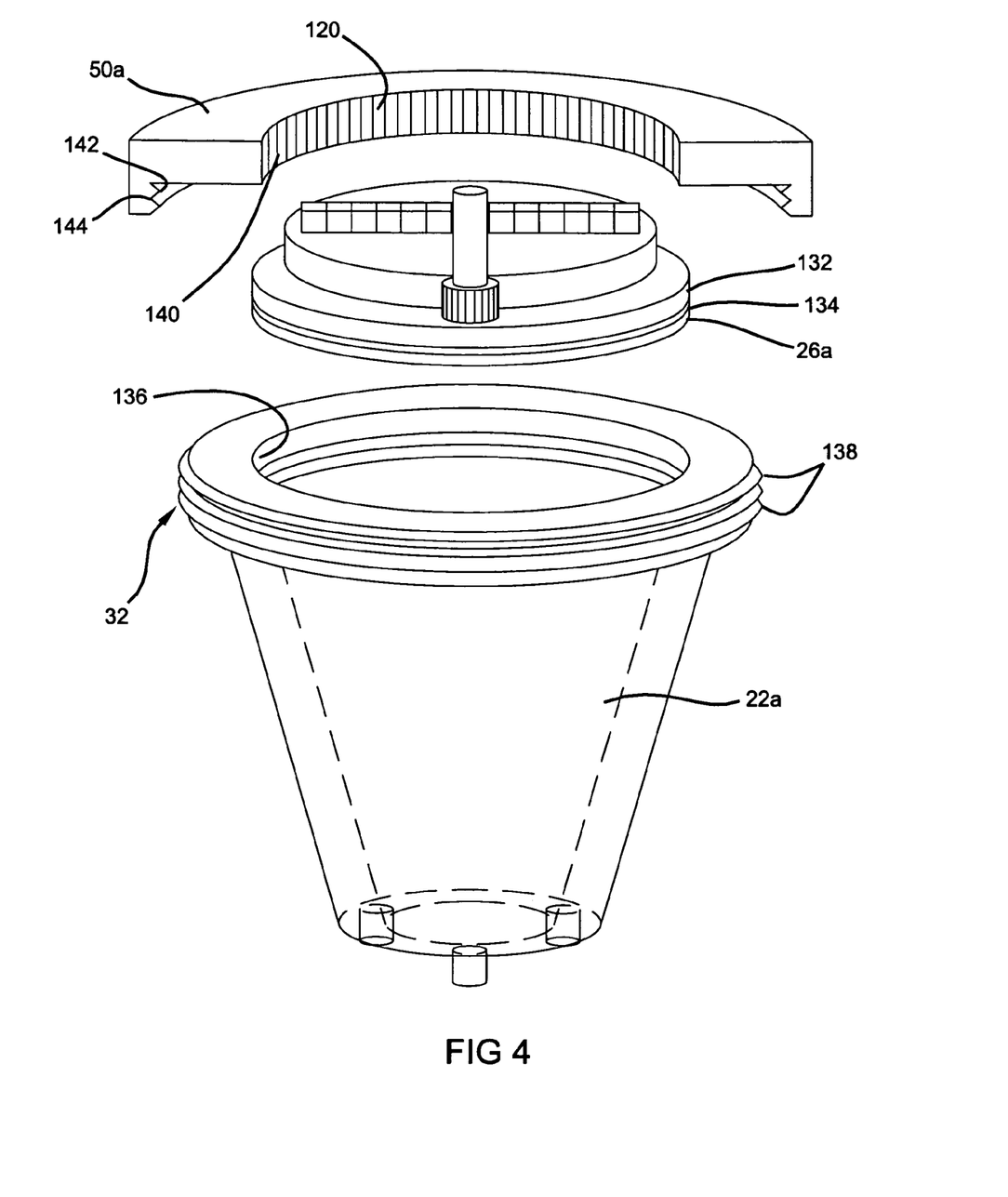
FIG. 4 is a partial detailed schematic view of an alternate preferred embodiment of the present invention having a vertical sealing configuration.

In an alternate preferred embodiment according to the present invention shown in FIG. 4, a retaining ring 50a and sealing configuration are in a vertical orientation in comparison with the horizontal configuration in the previous embodiment. The stage 26a has a peripheral vertical sealing edge 132, with a channel or groove therein for holding an O-ring type seal 134. The support structure 22a beneath has a mating vertical circular interior surface 136 which will contact the stage sealing edge 132, when the stage 26a and support structure 22a are coupled. The O-ring seal 134 will form a fluid-tight seal between the stage 26a and the support structure 22a. The exterior circumference of the proximal end 32 of the support structure 22 has a plurality of threads 138 formed therein. The retaining ring 50a itself has an inner circumference surface 140, which comprises the stationary gear ring. A lower surface region 142 of the retaining ring 50a has a plurality of threads 144 to engage the plurality of threads 138 formed in the exterior circumference of the support structure 22a. The retaining ring 50a may thus be threaded or screwed onto the support structure 22a, and clamps the stage 26a to the support structure 22a, securing them together. The present embodiment functions in all other respects in the same manner as described in the previous embodiments.

The present invention further provides a method for non-destructive ultrasonic testing of a target. The method entails positioning an ultrasonic detection assembly over a target surface. A proximal end of the detection assembly is contacted with a target surface. An ultrasonic transducer transmits ultrasonic waves through the proximal end to the target. Any ultrasonic waves reflected from the target are registered at the transducer. Lastly, the transducer moves to reposition the transducer. At the new position, another scan is repeated in the same manner as listed above. This method may be repeated multiple times to generate a plurality of B-Scan cross-sections which can be compiled to generate a three-dimensional image of the target.

In preferred embodiments of the present invention, the moving comprises rotating the transducer relative to the proximal end, where the rotating is conducted by a drive mechanism to rotationally reposition the transducer. Also, the positioning preferably comprises positioning the transducer relative to a first area of the target. The transducer is moved to reposition the transducer to a second area of the target, the second area being distinct from the first area, preferably a different rotational position to generate the plurality of cross-sectional scans.

In certain preferred embodiments of the method according to the present invention, the moving of the transducer is conducted while maintaining contact between the terminal surface of the support structure and the target. In alternate preferred embodiments, while the transducer is moved, it may be lifted off the target surface. After the transducer is moved to a new position, contact between the terminal end and the target is re-established.

The rotational movement of the present invention provides several advantages over traditional translational scanning employed with liner phased arrays. The assembly can be more compact (by roughly $$\frac{1}{\sqrt{2}})$$

because it eliminates the necessity to cover the corners of a square image, which generally do not contain useful information. Secondly, the preferred embodiments of the present invention use the direct rotational movement of a motor, without the need for translating the rotary motion into linear motion (e.g. eliminating ball and screw or rack and pinion mechanisms and support guides). Further, a circular shaped assembly is easier to seal than rectangular shaped devices. Another preferred aspect of the present invention is enhanced ultrasonic inspection that optimizes the scanning area while having a compact and robust assembly, to enable the use of accurate non-destructive testing for quality control.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An ultrasonic inspection assembly comprising:
   an ultrasonic transducer mounted on a stage;
   a support structure having a proximal end adjacent to said stage and a terminal end opposite to said stage, said support structure defining an interior space filled with a media which transmits ultrasonic waves, wherein said transducer is arranged to direct ultrasonic waves through said media to said terminal end and then to a target comprising a resistance spot weld joint;
   wherein said stage and said proximal end of said support structure are coupled to one another, and said transducer is oriented such that it transmits ultrasonic waves through said media; and
   a drive mechanism for rotating one of said stage and said support structure relative to the other one of said stage and said support structure.

2. The ultrasonic inspection assembly of claim 1 wherein said stage rotates relative to said support structure.

3. The ultrasonic inspection assembly of claim 1 wherein said media is water.

4. The ultrasonic inspection assembly of claim 1 wherein said interior space within said support structure has a distance from said proximal end to said terminal end that optimizes a shape of an ultrasonic beam emitted from said transducer.

5. The ultrasonic inspection assembly of claim 1 wherein said stage and said support structure are coupled to one another by a coupling that comprises a seal to prevent or at least minimize leakage of fluid from said proximal end of said interior space to an exterior of the assembly.

6. The ultrasonic inspection assembly of claim 1 wherein at least a portion of said terminal end is in contact with a target.

7. The ultrasonic inspection assembly of claim 1 wherein said terminal end is substantially sealed from fluid communication from said interior space to an exterior of the assembly by a seal.

8. The ultrasonic inspection assembly of claim 7 wherein said seal of said terminal end comprises a compliant polymeric material diaphragm.

9. The ultrasonic inspection assembly of claim 8 wherein at least a portion of said diaphragm is in direct contact with a target.

10. The ultrasonic inspection assembly of claim 1 wherein said terminal end has an aperture to permit a small continuous flow that establishes a continuous path of said media from said terminal end to a target.

11. The ultrasonic inspection assembly of claim 1 wherein said stage is coupled to said support structure by a retaining ring, said retaining ring having an interior circumference comprising a ring gear, and said drive mechanism comprising a pinion which traverses along said ring gear to provide rotational movement of said stage relative to said support structure.

12. The ultrasonic inspection assembly of claim 1 wherein said ultrasonic transducer is a high-frequency linear phased array ultrasonic transducer.

13. The ultrasonic inspection assembly of claim 1 wherein said support structure has a length of less than about 25 mm.

14. An ultrasonic inspection assembly for testing resistance spot welds comprising:
   a high frequency linear phased array ultrasonic transducer mounted on a stage;
   a support structure having a proximal end adjacent to said stage and a terminal end opposite to said stage and in contact with a resistance spot weld target, said support structure defining an interior space filled with a media which transmits ultrasonic waves, wherein said transducer is arranged to direct ultrasonic waves through said media to said spot weld target, wherein said stage and said proximal end of said support structure are coupled to one another; and
   a drive mechanism for rotating said stage relative to said support structure.

15. An ultrasonic inspection assembly comprising:
   an ultrasonic transducer mounted on a stage;
   a support structure having a proximal end adjacent to said stage and a terminal end opposite to said stage, said support structure defining an interior space filled with a media which transmits ultrasonic waves, wherein said terminal end has an aperture to permit a small continuous flow that establishes a continuous path of said media from said terminal end to a target, wherein said transducer is oriented such that it transmits ultrasonic waves through said media; and
   a drive mechanism for rotating one of said stage and said support structure relative to the other one of said stage and said support structure.

* * * * *